United States Patent [19]

Berthe

[11] Patent Number: 5,678,263
[45] Date of Patent: Oct. 21, 1997

[54] ECHOCARDIOGRAPHIC EXAMINATION TABLE

[76] Inventor: Christian Berthe, Avenue des Ormes 29, 4000 Liège, Belgium

[21] Appl. No.: 564,287
[22] PCT Filed: Apr. 19, 1995
[86] PCT No.: PCT/BE95/00037
  § 371 Date: Feb. 28, 1996
  § 102(e) Date: Feb. 28, 1996
[87] PCT Pub. No.: WO95/28882
  PCT Pub. Date: Nov. 2, 1995

[30] Foreign Application Priority Data

Apr. 20, 1994 [BE] Belgium .................. 09400406

[51] Int. Cl.⁶ ........................................ A61G 7/00
[52] U.S. Cl. ................ 5/600; 5/601; 5/624; 5/613
[58] Field of Search ................. 5/889, 602, 607, 5/613, 614, 617, 624; 128/845; 482/57

[56] References Cited

U.S. PATENT DOCUMENTS

| | | | |
|---|---|---|---|
| 3,584,321 | 6/1971 | Buchanan | 5/601 |
| 3,599,963 | 8/1971 | Grover | 5/600 X |
| 3,750,479 | 8/1973 | Gause et al. | 482/57 X |
| 3,814,414 | 6/1974 | Chapa | 5/607 X |
| 4,285,515 | 8/1981 | Gezari | 5/617 X |
| 5,342,261 | 8/1994 | Johnston | 482/57 |
| 5,461,739 | 10/1995 | Falbo, Sr. | 5/607 |

*Primary Examiner*—Michael F. Trettel
*Attorney, Agent, or Firm*—Sughrue, Mion, Zinn, Macpeak & Seas, PLLC

[57] ABSTRACT

A table with a top panel 10 attached to a frame 14 mounted on runners and slidable along a supporting underframe 16 on a base. The top panel consists of a back rest 11 and a seat 12 mutually pivotable about a hinge 13 fastened to the frame. The back rest and the seat are connected to devices 17, 18 attached to the underframe for adjusting the tilt of the back rest and the seat. The ends of the underframe are mounted on two posts so that it is tiltable thereon about a longitudinal pivot axis, and a pedal assembly 20 is attached to said underframe.

8 Claims, 3 Drawing Sheets

ECHOCARDIOGRAPHIC EXAMINATION TABLE

BACKGROUND OF THE INVENTION

The present invention relates to a table intended for being used to carry out rest and exercise echocardiographic examinations.

Usual echocardiographic tables comprise a horizontal couch mounted on a structure fitted with casters and a crank gear fixed to the couch and which the patient sets in motion with his legs for exercise echocardiographic examinations. As the patient lies horizontally on his back, the movement of his legs must be done in uncomfortable conditions and it is necessary to provide for additional accessories in order to ensure the immobilization of the patient's thorax.

SUMMARY OF THE INVENTION

It is the object of the invention to provide a compact table requiring minimum space and making it possible to carry out both rest and exercise examinations in maximum conditions of comfort while ensuring a great stability of the patient's thorax and thus a persistence of the quality of the echocardiographic image during the exercise.

More particularly, the couch is attached to a frame mounted on sliding-blocks arranged to slide lengthwise on a carrying chassis fixed to a support structure. The couch is comprised of a back and a seat attached so as to be capable of pivoting on a hinge axis fixed to the frame. The back and the seat are connected to means fixed to the carrying chassis in order to adjust the back and the seat inclines. The carrying chassis is mounted at its ends on two supporting columns so as to be rotatable on a longitudinal pivot axis. The crank gear is attached to the carrying chassis and it can be connected to a driving device for the control of the height thereof in relation to the carrying chassis.

BRIEF DESCRIPTION OF THE FIGURES

The features and advantages of the invention will become more readily apparent from the following description of an exemplary embodiment represented in the accompanying drawings.

DETAILED DESCRIPTION OF THE PREFERRED EMBODIMENT

Figure 1:
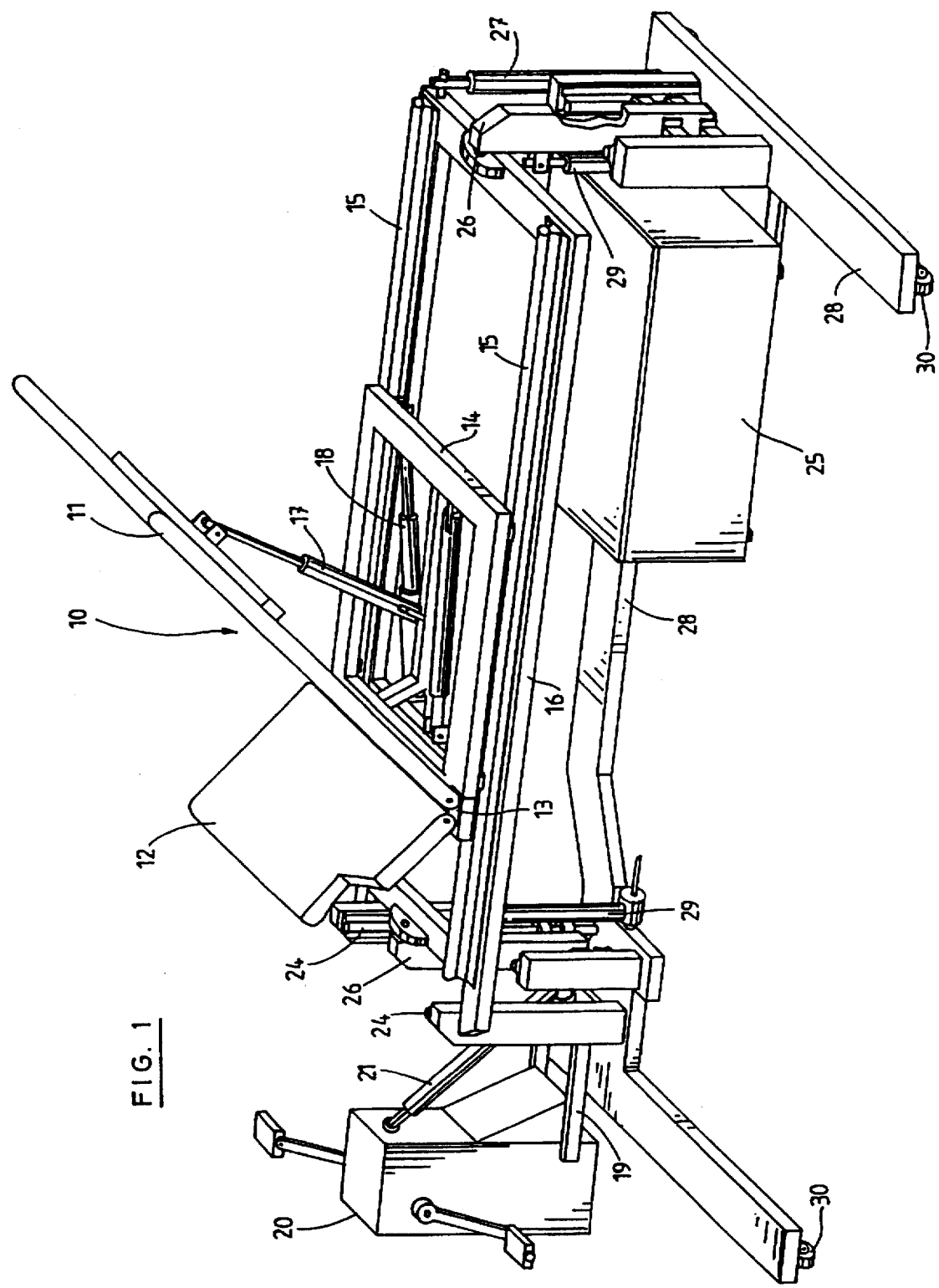
FIG. 1 is a perspective view of an echocardiographic examination table according to the invention in an examination position.
Figure 2:
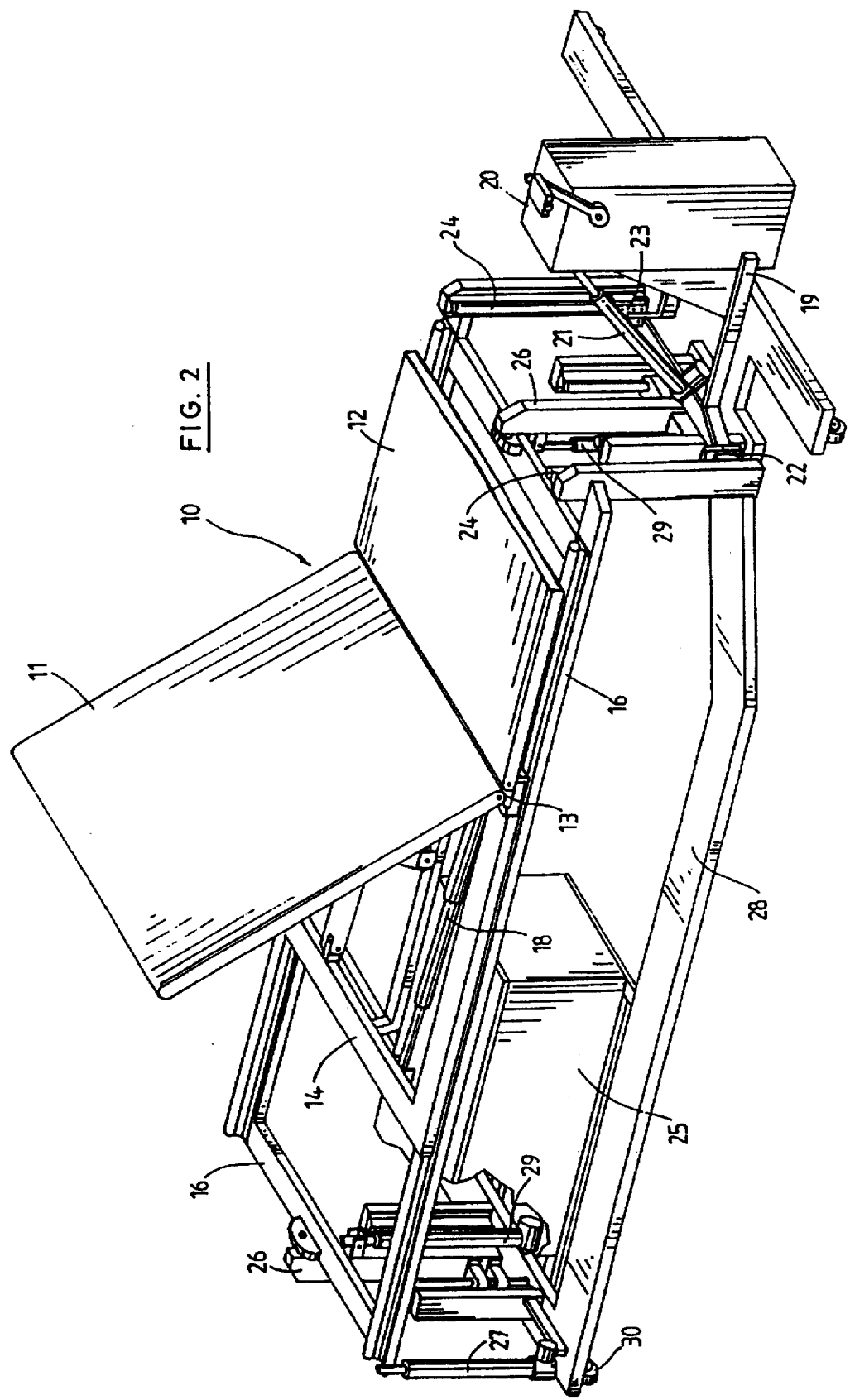
FIG. 2 is a perspective view of the table shown in FIG. 1 in a waiting position.

As shown in the drawings, the couch 10 of the examination table according to the invention is comprised of a back 11 and a seat 12 connected by a hinge 13 that allows the back 11 on the one hand and the seat 12 on the other hand to be inclined separately. Hinge 13 is fixed to a metallic frame 14 mounted on sliding-blocks capable of sliding on two parallel rails 15 fixed to the longitudinal sides of a carrying chassis 16. When the frame 14 moves along rails 15, the back 11 and the seat 12 move in a front back movement in relation to the chassis. Jacks 17 and 18 are fixed to frame 14 for the control of the individual inclinations of the back 11 and the seat 12 respectively.

To the carrying chassis 16 there is also attached a fork 19 carrying a crank gear 20 which is thereby movable together with the chassis during its lateral revolving movement. The crank gear 20 is connected to a jack 21 which permits the crank gear to be moved independently in an upward and adjustable movement relative to the chassis 16. The crank gear is advantageously connected to an electronic device 25 arranged to perform programmes of progressive difficulty in order to graduate the efforts to be made by the patient.

Figure 3:
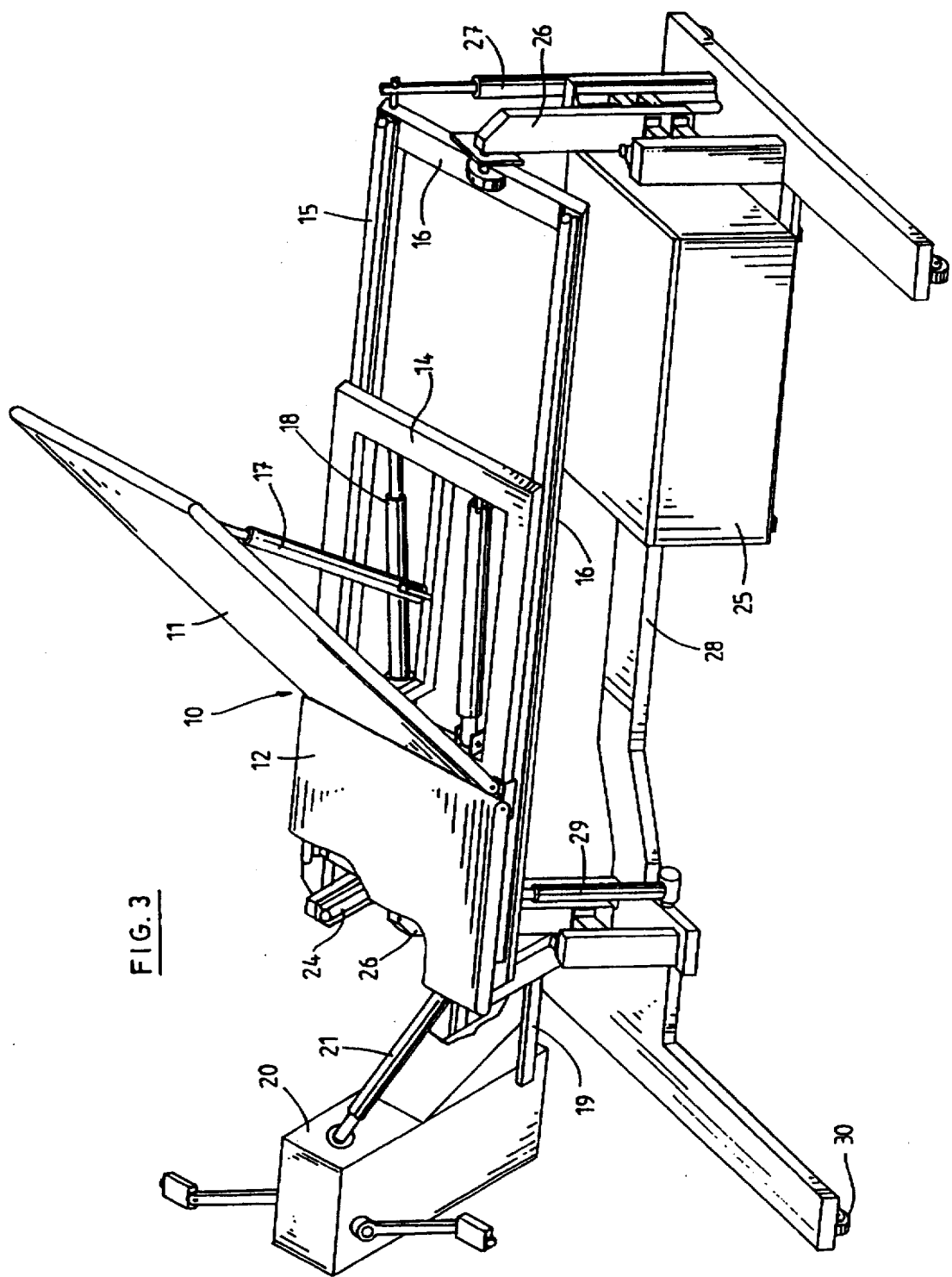
FIG. 3 is a perspective view of the table represented in FIG. 1, with the chassis shown in a rotated position to the left.

Carrying chassis 16 is comprised of longitudinal girders linked at their ends by transverse girders. These are fixed in their middle portion to two supporting columns 26 so as to be capable of revolving on a longitudinal pivot axis 100, whereby the chassis moves the back 11 and the seat 12 in a lateral revolving movement on the anterio-posterior axis of the table (see FIG. 3). The rotation of the chassis on the anterio-posterior axis mentioned above is controlled by jack 27 connected between the chassis 16 and the table support structure 28.

The supporting columns 26 are fixed to the support structure 28 fitted with casters 30. The columns 26 are provided with jacks 29 which permit the chassis 16 and the assembly it carries to be moved upwardly in relation to the table support structure.

The table according to the invention makes it possible to perform exercise echocardiographic examinations in conditions of maximum comfort for the patient who can rest in a semi-lying position. The back 11 can be inclined advantageously by an angle of about 45° relative to the horizontal plan and the seat 12 can be advantageously inclined by angle of about 30°. In addition, the patient's position relative to the crank gear can be adjusted accurately and rapidly by the back and the seat being moved in an anterio-posterior horizontal sliding movement. By being moved upwardly, the crank gear can be positioned in height perfectly in order to reduce to a minimum the tiredness of the lower limbs of the patient while taking exercise.

This comfortable position for the patient enables him to make a maximum effort while avoiding the rapid tiredness of the lower limbs and the parasitic movement of the thorax. Thus, the echocardiographic image is always of an excellent quality and perfectly stable. By virtue of the table allowing the patient to remain motionless, it would be possible to provide the table with a probe carrier for echocardiographic measurements.

The height control of the chassis and the assembly it carries makes it possible to perform examinations to the left or to the right of the patient depending on the examiner's habits.

The examination table according to this invention further comprises an electric control panel (not represented) which houses the controls for all the travellings and movements of the structure elements and the controls of the exercises programmes.

When the crank gear is in a low position and the seat in a horizontal position, the table allows a rest echocardiographic examination to be performed provided that a short extension piece be placed to rest on the top of the crank gear block.

I claim:

1. An examination table, comprising:
   (i) a support structure (28);
   (ii) an elongate carrying chassis (16) fixed to the support structure and having first and second ends;
   (iii) frame means (14) mounted on sliding-blocks capable of sliding movement lengthwise of the carrying chassis;

(iv) couch means (10) attached to said frame means, said couch means having a back portion (11) and a seat portion (12) pivotally connected to hinge means (13) fixed to said frame means so as to be capable of pivoting individually relative to said frame means;

(v) drive means (17, 18) fixed to the carrying chassis and connected to said back portion and said seat portion for adjustably positioning an angular inclination of the back and seat portions; and (vi) crank gear means (20) attached to said carrying chassis in a position adjacent one of said ends of the carrying chassis.

(vii) wherein the carrying chassis is mounted at its ends on two support columns (26) so as to be capable of revolving on a longitudinal pivot axis.

2. An examination table, comprising:

(i) a support structure (28);

(ii) an elongate carrying chassis (16) fixed to the support structure and having first and second ends;

(iii) frame means (14) mounted on sliding-blocks capable of sliding movement lengthwise of the carrying chassis;

(iv) couch means (10) attached to said frame means, said couch means having a back portion (11) and a seat portion (12) pivotally connected to hinge means (13) fixed to said frame means so as to be capable of pivoting individually relative to said frame means;

(v) drive means (17, 18) fixed to the carrying chassis and connected to said back portion and said seat portion for adjustably positioning an angular inclination of the back and seat portions; and (vi) crank gear means (20) attached to said carrying chassis in a position adjacent one of said ends of the carrying chassis.

(vii) wherein the carrying chassis is connected to driving means (29) for the control of its height in relation to the support structure.

3. An examination table, comprising:

(i) a support structure (28);

(ii) an elongate carrying chassis (16) fixed to the support structure and having first and second ends;

(iii) frame means (14) mounted on sliding-blocks capable of sliding movement lengthwise of the carrying chassis;

(iv) couch means (10) attached to said frame means, said couch means having a back portion (11) and a seat portion (12) pivotally connected to hinge means (13) fixed to said frame means so as to be capable of pivoting individually relative to said frame means;

(v) drive means (17, 18) fixed to the carrying chassis and connected to said back portion and said seat portion for adjustably positioning an angular inclination of the back and seat portions; and (vi) crank gear means (20) attached to said carrying chassis in a position adjacent one of said ends of the carrying chassis.

(vii) wherein the crank gear (20) is connected to driving means (21) for the control of its height in relation to said carrying chassis.

4. An examination table, comprising:

(i) a support structure (28);

(ii) an elongate carrying chassis (16) fixed to the support structure and having first and second ends;

(iii) frame means (14) mounted on sliding-blocks capable of sliding movement lengthwise of the carrying chassis;

(iv) couch means (10) attached to said frame means, said couch means having a back portion (11) and a seat potion (12) pivotally connected to hinge means (13) fixed to said frame means so as to be capable of pivoting individually relative to said frame means;

(v) drive means (17, 18) fixed to the carrying chassis and connected to said back portion and said seat portion for adjustably positioning an angular inclination of the back and seat portions; and (vi) crank gear means (20) attached to said carrying chassis in a position adjacent one of said ends of the carrying chassis.

(vii) wherein the crank gear (20) is connected to means (25) for performing programs of progressive difficulty.

5. An examination table as claimed in claim 2, 3 or 4, wherein the carrying chassis is mounted at its ends on two support columns (26) so as to be capable of revolving on a longitudinal pivot axis.

6. An examination table as claimed in claim 1, 3 or 4, wherein the carrying chassis is connected to driving means (29) for the control of its height in relation to the support structure.

7. An examination table as claimed in claim 1, 2 or 4, wherein the crank gear (20) is connected to driving means (21) for the control of its height in relation to said carrying chassis.

8. An examination table as claimed in claims 1, 2, 3, wherein the crank gear (20) is connected to means (25) for performing programs of progressive difficulty.

* * * * *